United States Patent
Tseng et al.

(10) Patent No.: US 7,016,790 B2
(45) Date of Patent: Mar. 21, 2006

(54) IN-LINE HOT-WIRE SENSOR FOR SLURRY MONITORING

(75) Inventors: Tung-Ching Tseng, Taipei (TW); Li-Jia Yang, Hsin-Chu (TW)

(73) Assignee: Taiwan Semiconductor Manufacturing Co., Ltd., Hsin Chu (TW)

( * ) Notice: Subject to any disclaimer, the term of this patent is extended or adjusted under 35 U.S.C. 154(b) by 118 days.

(21) Appl. No.: 10/279,575

(22) Filed: Oct. 23, 2002

(65) Prior Publication Data

US 2004/0083068 A1    Apr. 29, 2004

(51) Int. Cl.
*G01N 31/00* (2006.01)

(52) U.S. Cl. .................. 702/25; 702/32; 73/861.04; 73/204.27; 451/41; 451/28; 451/287

(58) Field of Classification Search .......... 702/22–32, 702/50, 100, 133, 182, 183, 185; 73/861.04, 73/204.27, 67.41; 451/28, 41, 287; 324/439, 324/717
See application file for complete search history.

(56) References Cited

U.S. PATENT DOCUMENTS

| | | | |
|---|---|---|---|
| 4,317,178 A * | 2/1982 | Head ............................ 702/47 |
| 4,334,186 A * | 6/1982 | Sasayama et al. ........... 323/365 |
| 4,433,576 A * | 2/1984 | Shih et al. ................. 73/204.21 |
| 4,458,529 A * | 7/1984 | Nagaishi et al. .......... 73/204.18 |
| 4,587,842 A * | 5/1986 | Handtmann .............. 73/204.14 |
| 4,648,271 A * | 3/1987 | Woolf ....................... 73/204.27 |
| 4,658,654 A * | 4/1987 | Ozaki et al. .............. 73/861.05 |
| 5,056,928 A * | 10/1991 | Aoki et al. ..................... 374/16 |
| 5,225,126 A * | 7/1993 | Alles et al. .................. 264/620 |
| 5,297,438 A * | 3/1994 | Alles et al. .................... 73/727 |
| 5,681,989 A * | 10/1997 | Kanke et al. ............... 73/118.2 |
| 5,756,898 A * | 5/1998 | Diatschenko et al. ......... 73/592 |
| 5,934,974 A * | 8/1999 | Tzeng ............................ 451/6 |
| 6,019,946 A * | 2/2000 | Castillo et al. ............... 422/94 |
| 6,077,783 A * | 6/2000 | Allman et al. .............. 438/691 |
| 6,122,956 A * | 9/2000 | Klausner et al. ........... 73/61.71 |
| 6,183,656 B1 * | 2/2001 | Ide et al. ...................... 216/85 |
| 6,327,905 B1 * | 12/2001 | Itsuji et al. ............... 73/204.15 |
| 6,378,378 B1 * | 4/2002 | Fisher ......................... 73/754 |
| 6,431,953 B1 * | 8/2002 | Carter et al. ................... 451/5 |
| 6,457,852 B1 * | 10/2002 | Hiraoka et al. ............. 366/136 |
| 6,619,142 B1 * | 9/2003 | Forster et al. ........... 73/861.74 |
| 6,684,695 B1 * | 2/2004 | Fralick et al. ........... 73/204.26 |
| 2001/0045121 A1 * | 11/2001 | Chiba et al. ............... 73/25.02 |
| 2002/0173223 A1 * | 11/2002 | Gitis et al. ...................... 451/5 |
| 2003/0056584 A1 * | 3/2003 | Park ......................... 73/204.11 |
| 2003/0119197 A1 * | 6/2003 | Bonne et al. ............... 436/149 |
| 2003/0217737 A1 * | 11/2003 | Ismailov ..................... 123/494 |
| 2004/0038623 A1 * | 2/2004 | Chandrasekaran ............. 451/5 |

OTHER PUBLICATIONS

"Word IQ", www.wordiq.com, copyright 2004.
"A very Basic Introduction to Time/Frequency Domains", www.theparticle.com/cs/mcs/signalnotes.pdf, Mar. 10, 2004.

* cited by examiner

*Primary Examiner*—Carol S. W. Tsai
(74) *Attorney, Agent, or Firm*—Tung & Associates

(57) ABSTRACT

An in-line hot-wire sensor for monitoring the mixing and the flow rate of slurry is disclosed. The hot-wire sensor may include a number of resistors organized into a Wheatstone bridge, as well as a frequency-domain transform mechanism. The resistors include a hot-wire resistor that is placed in-line with the slurry after substances have been mixed to become the slurry. The Wheatstone bridge thus yields a signal that is transformed to the frequency domain by the frequency-domain transform mechanism, such as by performing a Fast Fourier Transform (FFT) of the signal. The frequency-domain transform is used to monitor the mixing of the substances into the slurry, and the flow rate of the slurry. The signal may be amplified prior to transformation to the frequency domain.

5 Claims, 4 Drawing Sheets

IN-LINE HOT-WIRE SENSOR FOR SLURRY MONITORING

FIELD OF THE INVENTION

This invention relates generally to slurry, such as that used in chemical-mechanical polishing (CMP), and more particularly to monitoring the slurry, such as monitoring its flow rate and monitoring the mixture of substances to the slurry.

BACKGROUND OF THE INVENTION

Chemical mechanical polishing (CMP) is a semiconductor wafer flattening and polishing process that combines chemical removal with mechanical buffing. It is used for polishing and flattening wafers after crystal growing, and for wafer planarization during the wafer fabrication process. CMP is a favored process because it can achieve global planarization across the entire wafer surface, can polish and remove all materials from the wafer, can work on multi-material surfaces, avoids the use of hazardous gasses, and is usually a low-cost process.

FIGS. 1A and 1B show an example effect of performing CMP. In FIG. 1A, a semiconductor wafer 102 has a patterned dielectric layer 104, over which a metal layer 106 has been deposited. The metal layer 106 has a rough top surface, and there is more metal than necessary. Therefore, CMP is performed, resulting in FIG. 1B. In FIG. 1B, the metal layer 106 has been polished down so that it only fills the gaps within the dielectric layer 104.

FIG. 2 shows an example CMP system 200 for polishing the wafer 102 of FIGS. 1A and 1B. The wafer 102, with its dielectric layer 104 and metal layer 106, is placed on a platen 202 connected to a rotatable rod 206. A polishing pad 204 is lowered over the wafer 102, specifically over the metal layer 106 thereof. The polishing pad 204 is also connected to a rotatable rod 206. Slurry 210 is introduced between the polishing pad 204 and the metal layer 106, and the polishing pad 204 is lowered, pressured against the metal layer 106, and rotated to polish away the excess, undesired metal from the metal layer 106. The platen 202 is rotated as in the opposite direction. The combined actions of the two rotations and the abrasive slurry 210 polish the wafer surface.

The polishing pad 204 can be made of cast polyurethane foam with fillers, polyurethane impregnated felts, or other materials with desired properties. Important pad properties include porosity, compressibility, and hardness. Porosity, usually measured as the specific gravity of the material, governs the pad's ability to deliver slurry in its pores and remove material with the pore walls. Compressibility and hardness relate to the pad's ability to conform to the initial surface irregularities. Generally, the harder the pad is, the more global the planarization is. Softer pads tend to contact both the high and low spots, causing non-planar polishing. Another approach is to use flexible polish heads that allow more conformity to the initial wafer surface.

The slurry 210 has a chemistry that is complex, due to its dual role. On the mechanical side, the slurry is carrying abrasives. Small pieces of silica are used for oxide polishing. Alumina is a standard for metals. Abrasive diameters are usually kept to 10–300 nanometers (nm) in size, to achieve polishing, as opposed to grinding, which uses larger diameter abrasives but causes more surface damage. On the chemical side, the etchant may be potassium hydroxide or ammonium hydroxide, for silicon or silicon dioxide, respectively. For metals such as copper, reactions usually start with an oxidation of the metal from the water in the slurry. Various additives may be found in slurries, to balance their ph, to establish wanted flow characteristics, and for other reasons.

FIG. 3 shows an example slurry mixing and delivery system 300 that may be used to mix and delivery the slurry 210 in-line to the CMP system 200 of FIG. 2. There are two intake pipes, a first pipe 302 and a second pipe 304. The first pipe 302 may be used to input abrasives, whereas the second pipe 304 may be used to input additives, such as surfactants and/or other additives. A surfactant is generally a substance capable of reducing the surface tension of a liquid in which it is dissolved. At the point 306 where the pipes 302 and 304 meet, the abrasives and the additives are mixed, such that there is a single flow of slurry in the connecting pipe 308. The pipe 308 ends in a nozzle 310 that outputs the slurry to the CMP system.

Slurry mixing, however, is vulnerable to certain problems. One problem is poor mixing of the abrasives and the additives. Optimally, the abrasives and the additives mix into a homogenous slurry mixture. However, at least occasionally the abrasives and the additives do not mix into a homogenous slurry mixture, which can result in non-optimal CMP to occur. Another problem is unstable slurry flow. If the slurry flow is not maintained at a steady and stable flow rate, or when the transient response of the slurry flow varies over time, non-optimal CMP can also occur. Currently, however, there is no adequate mechanism to conduct inline of monitoring the slurry mixing and delivery, to detect these and other problems.

Therefore, there is a need for in-line monitoring of slurry mixing and delivery. Such monitoring should be able to detect when the abrasives and the additives do not mix into a homogenous slurry mixture. Such monitoring should also be able to detect when there is an unstable slurry flow. For these and other reasons, there is a need for the present invention.

SUMMARY OF THE INVENTION

The invention relates to an in-line hot-wire sensor for monitoring the mixing and the flow rate of slurry. The hot-wire sensor may include a number of resistors organized into a Wheatstone bridge, as well as a frequency-domain transform mechanism. The resistors include a hot-wire resistor that is placed in-line with the slurry after substances have been mixed to become the slurry. The Wheatstone bridge thus yields a signal that is transformed to the frequency domain by the frequency-domain transform mechanism, such as by performing a Fast Fourier Transform (FFT) of the signal. The frequency-domain transform is used to monitor the mixing of the substances into the slurry, and the flow rate of the slurry. The signal may be amplified prior to transformation to the frequency domain.

Embodiments of the invention provide for advantages over the prior art. The hot-wire resistor has a fast response time to variations in slurry flow rate, and to variations in the mixing of substances into slurry. As a result, the output signal of the Wheatstone bridge also is responsive in a fast manner to these variations. The frequency-domain transform of the signal allows for convenient analysis of the output signal, to determine whether such variations are taking place. Other advantages, embodiments, and aspects of the invention will become apparent by reading the detailed description that follows, and by referencing the attached drawings.

BRIEF DESCRIPTION OF THE DRAWINGS

FIGS. 6A and 6B show proper slurry flow rate and mixing, and FIGS. 6C and 6D show improper slurry flow rate and/or improper slurry mixing.

DETAILED DESCRIPTION OF THE INVENTION

In the following detailed description of exemplary embodiments of the invention, reference is made to the accompanying drawings that form a part hereof, and in which is shown by way of illustration specific exemplary embodiments in which the invention may be practiced. These embodiments are described in sufficient detail to enable those skilled in the art to practice the invention. Other embodiments may be utilized, and logical, mechanical, and other changes may be made without departing from the spirit or scope of the present invention. The following detailed description is, therefore, not to be taken in a limiting sense, and the scope of the present invention is defined only by the appended claims. For instance, whereas the invention is substantially described in relation to the slurry used in a semiconductor fabrication chemical-mechanical polishing (CMP) tool, it is applicable to other semiconductor fabrication and other types of tools as well.

Figure 1A:
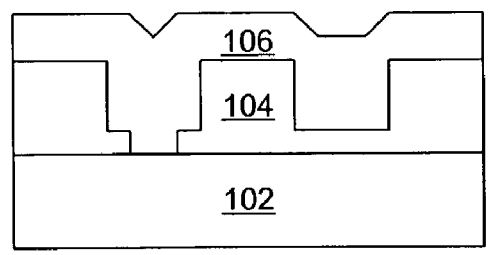
FIGS. 1A and 1B are diagrams showing an example chemical mechanical polishing (CMP) semiconductor fabrication operation.
Figure 1B:
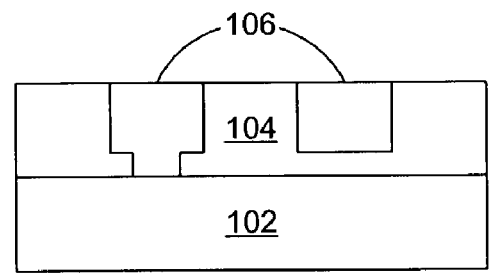
Figure 2:
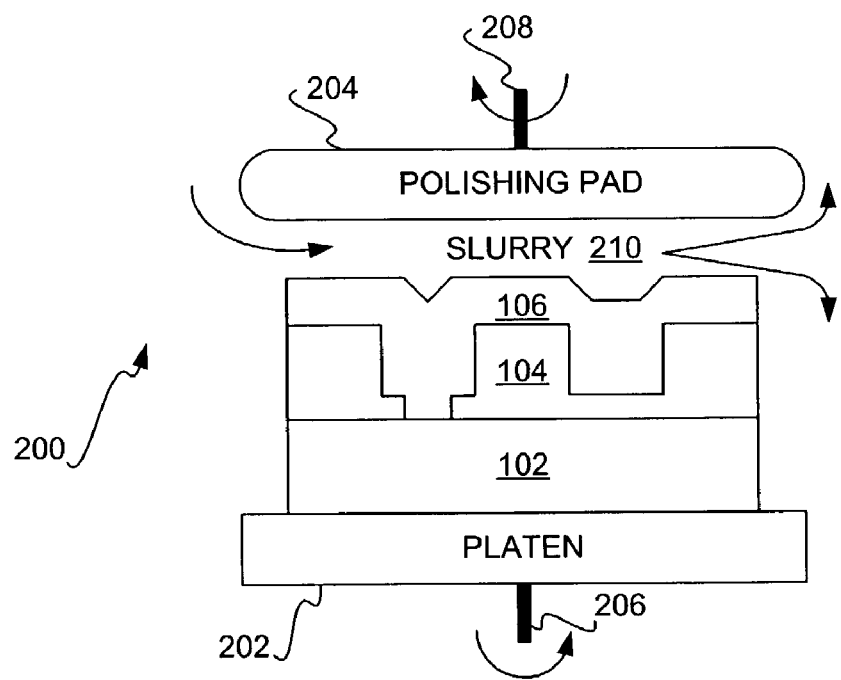
FIG. 2 is a diagram of an example CMP semiconductor fabrication system, in conjunction with which embodiments of the invention can be practiced.
Figure 3:
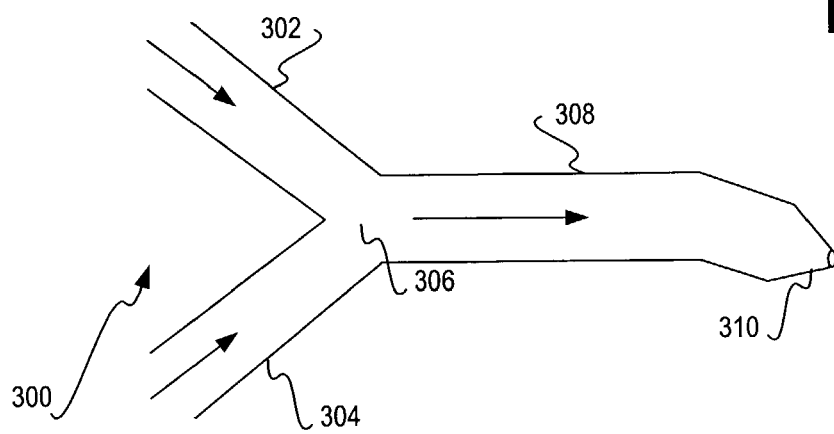
FIG. 3 is a diagram of an example slurry mixing and dispensing system in conjunction with which embodiments of the invention may be practiced.
Figure 4:
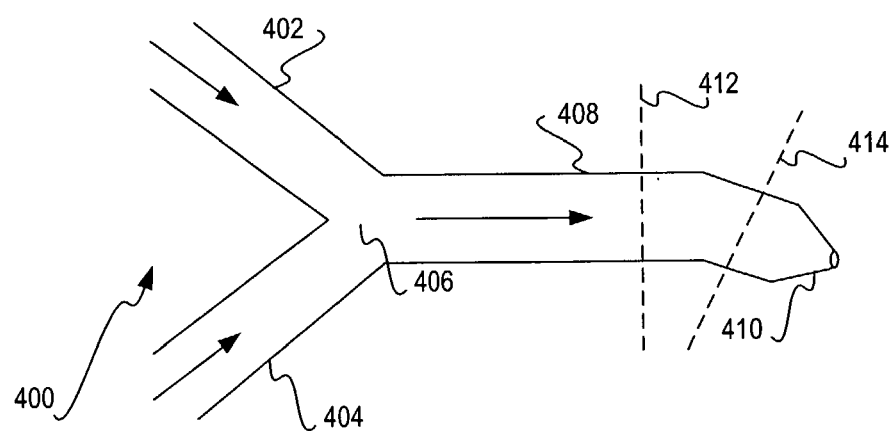
FIG. 4 is a diagram of an example slurry mixing and dispensing system, according to an embodiment of the invention, in which two positions in which a hot-wire sensor may be inserted are indicated.

FIG. 4 shows a system 400 according to an embodiment of the invention. Intake pipes 402 and 404 input substances, such as the substances that are used to make slurry for used with CMP. Whereas two of the intake pipes 402 and 404 are shown in FIG. 4, there may be more than two intake pipes. The intake pipes 402 and 404 meet at a point 406, so that the substances therein may be mixed into a slurry within the mix pipe 408. The term slurry may connotate the slurry used in CMP, but may be more generally the mixture of any other types of substances. The output pipe 408 ends in a dispensing nozzle 410. A sensor according to an embodiment of the invention is placed in-line with the slurry. For instance, it may be placed in the position indicated by the dotted line 412, within the mix pipe 408, or in the position indicated by the dotted line 414, within the dispensing nozzle 410.

Figure 5:
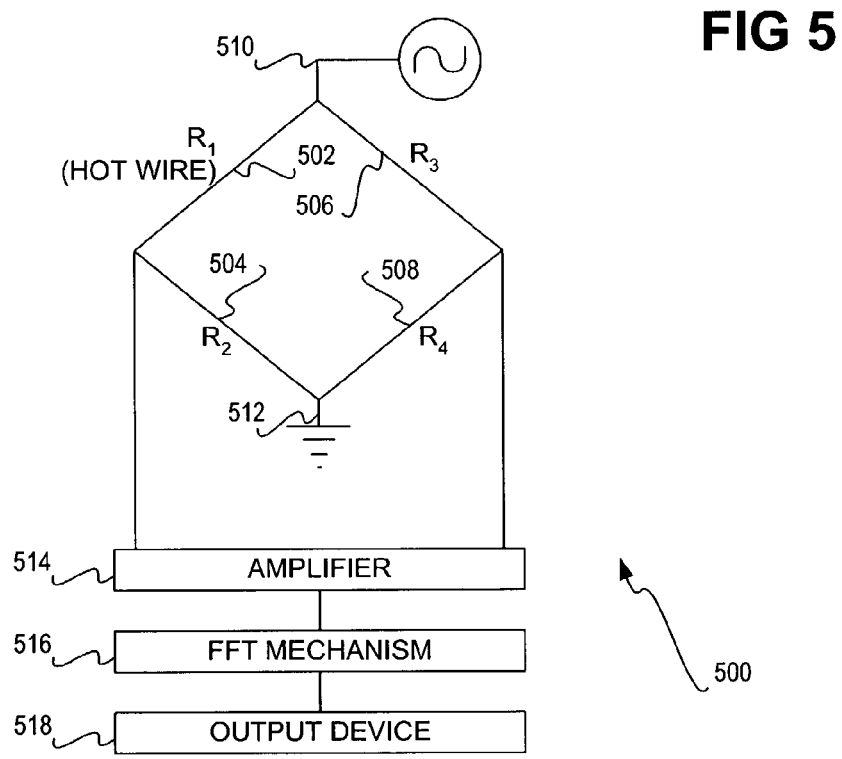
FIG. 5 is a diagram of a hot-wire sensor according to an embodiment of the invention that specifically utilizes a Wheatstone bridge.

FIG. 5 shows a sensor 500 according to an embodiment of the invention. At least some parts of the sensor 500 may be placed in the positions indicated by the dotted lines 412 and 414 of FIG. 4, within the system 400 of FIG. 4. The sensor is for monitoring the mixing of substances into the slurry, as well as for monitoring the flow rate of the slurry. The sensor 500 includes resistors 502, 504, 506, and 508 organized in a Wheatstone bridge configuration. Also included are a voltage source 510, a ground 512, and an amplifier that amplifies the voltage signal between two points within the Wheatstone bridge. The resistor 502 is specifically a hot wire that is placed in line with the slurry.

A Wheatstone bridge is an electrical bridge circuit used to measure resistance, and more specifically the precise comparison of resistances. The resistances of the resistors 504, 506, and 508 are known, whereas the resistance of the resistor 502 fluctuates, and thus is unknown. The parallel branch having the resistors 506 and 508 has a known resistance, whereas the parallel branch having the resistors 502 and 504 has an unknown resistance. If the resistance of the resistor 502 is desired to be determined, the resistances of the resistors 504, 506, and 508 are adjusted and balance until the current passing between the two branches—that is, the current passing within the amplifier 514—is zero. In other words, the Wheatstone bridge is well suited for the measurement of small changes of a resistance, and thus for the measurement of the resistance change of the hot wire resistor 502.

The resistor 502 is thus a hot-wire resistor, to make the sensor 500 a hot-wire sensor. The resistor 502 is more specifically a heated, thin wire, that when exposed to the flow field of the slurry, has a temperature dependent upon the heat rate, the wire diameter, the flow speed or rate of the slurry, and the properties of the slurry. The properties of the slurry include its mixture of the substances used to make the slurry. Thus, the properties of the slurry include whether this mixing is uniform or non-uniform, and so on. The resistance of the wire, in turn, is dependent on its temperature, making the resistor 502 a hot-wire resistor. The wire is heated by being loaded with a voltage, since when a thin, metal wire is loaded with a voltage, it generates heat.

The amplifier 514 amplifies the voltage signal between the two parallel branches, and this output signal is Fast Fourier Transformed (FFT'ed) by the FFT mechanism 516. The FFT mechanism 516 may be, for instance, a computer programmed for this purpose, or a combination of hardware and/or software designed for this purpose. The FFT is one type of frequency-domain transform. Other types of frequency-domain transforms, to transform the output signal that is inherently in the time domain to the frequency domain, may also be used. The FFT of the output signal is then output to an output device 518. The output device 518 may be a printer, a display device, or another type of device.

The FFT of the output signal transforms the voltage signal into the frequency domain. The FFT of the output signal is specifically responsive to high-frequency variations in the flow rate of the slurry, as well as to high-frequency variations in the mixing of the substances into the slurry. The response time of the output signal depends on the diameter and the properties of the hot wire resistor 502. The sensitivity of output voltage signal to variations in slurry flow rate and mixing depends on the configuration of the Wheatstone bridge, and the design of the amplifier 514. Furthermore, the response of the sensor, specifically the response of the hot wire resistor 502, to such variations is such that it can detect changes and variations within the range of a millisecond (ms).

Figure 6A:
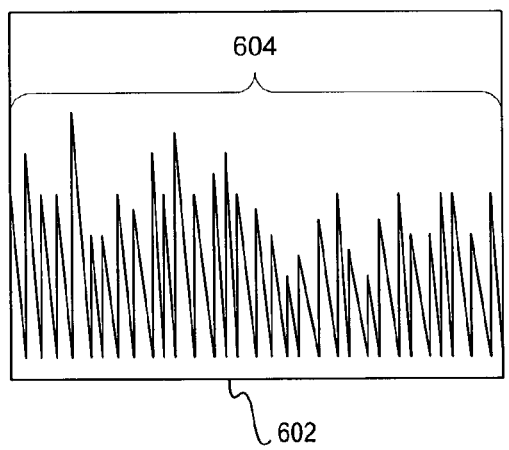
FIGS. 6A, 6B, 6C, and 6D are diagrams of frequency-domain plots as may be output by a hot-wire sensor of an embodiment of the invention, where
Figure 6B:
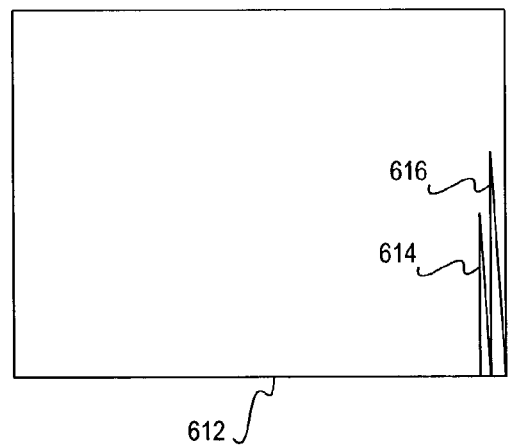

FIGS. 6A, 6B, 6C, and 6D show sample frequency domain plots that indicate proper and improper slurry flow rate and slurry mixing, resulting from the FFT of the output signal of the Wheatstone bridge. In FIG. 6A, the plot 602 shows white noise 604, indicating that the flow rate of the slurry, and the mixing of the substances into the slurry, is proper. That is, no one frequency response is significantly and pertinently greater than the other frequency responses, indicating proper flow rate and mixing. In FIG. 6B, the plot 612 shows two steady frequency response peaks 614 and 616. These peaks 614 and 616 correspond to a steady, pulsating pumping of slurry, indicating a proper flow rate of slurry.

Figure 6C:
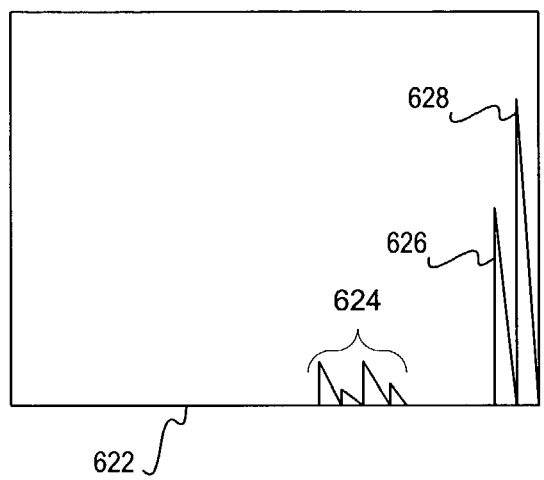
Figure 6D:
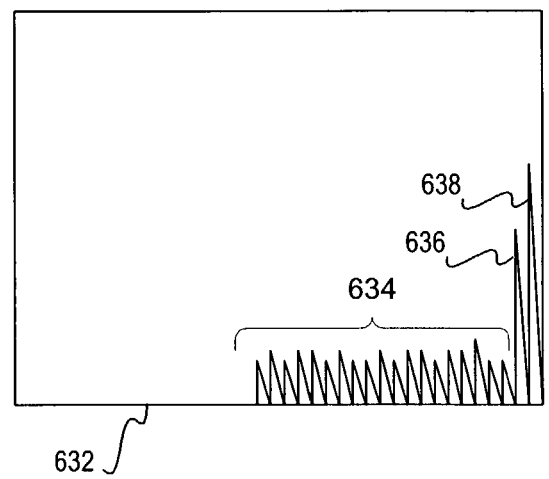

By comparison, the plots of FIGS. 6C and 6D show improper slurry flow rate and/or improper slurry mixing. In FIG. 6C, the plot 622 shows two small frequency response peaks 624, in addition to the two steady and large frequency response peaks 626 and 628. From prior experience, it is known that the peaks 626 and 628 correspond to the proper steady and pulsating pumping of slurry. However, the two small frequency response peaks 624 correspond to improper and poor slurry mixing. In FIG. 6D, the plot 632 shows a series of small frequency response peaks 634, in addition to the two steady and large frequency response peaks 636 and 638. As before, the peaks 636 and 638 correspond to proper pumping of slurry. However, the series of small frequency response peaks 634 correspond to the unsteady pumping of slurry, indicating a poor slurry flow rate.

Figure 7:
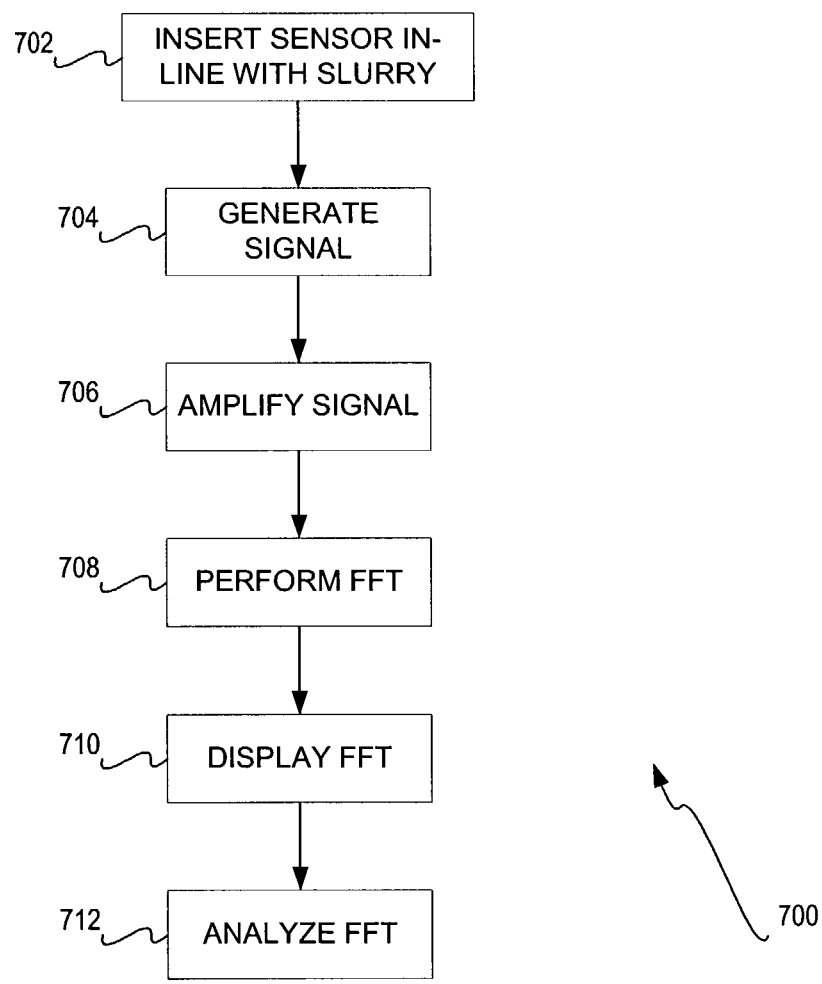
FIG. 7 is a method for monitoring slurry flow rate and mixing, according to an embodiment of the invention.

FIG. 7 shows a method 700 according to an embodiment of the invention, for monitoring slurry flow rate and slurry mixing. First, a hot-wire sensor is inserted in-line with the slurry, after substances have been mixed into the slurry (702). The hot-wire sensor may be the sensor as has been previously described in conjunction with FIG. 5. The hot-wire sensor generates a signal (704), such as a voltage signal. This time-domain signal is then amplified (706), and transformed to the frequency domain via performance of a FFT on the amplified time-domain signal (708). The FFT'ed signal is preferably displayed (710), and then analyzed (712) to determine whether proper slurry flow rate and slurry mixing are occurring. For instance, analysis can include examining the FFT'ed signal for unsteady variations indicative of the flow rate of the slurry being improper. Analysis can also include matching the FFT'ed signal to one or more reference FFT plots, such as the plots of FIGS. 6A, 6B, 6C, and 6D, to determine whether proper or improper slurry flow rate or slurry mixing is occurring.

It is noted that, although specific embodiments have been illustrated and described herein, it will be appreciated by those of ordinary skill in the art that any arrangement is calculated to achieve the same purpose may be substituted for the specific embodiments shown. This application is intended to cover any adaptations or variations of the present invention. For example, whereas the invention is substantially described in relation to the slurry used in a semiconductor fabrication chemical-mechanical polishing (CMP) tool, it is applicable to other semiconductor fabrication tools and other types of tools as well. Therefore, it is manifestly intended that this invention be limited only by the claims and equivalents thereof.

What is claimed is:

1. A system for monitoring slurry flow properties during a chemical mechanical polish (CMP) process comprising:
   a plurality of resistors comprising a Wheatstone bridge sensor, the Wheatstone bridge sensor positionable in a CMP polish slurry feed pathway;
   wherein at least one of the plurality of resistors comprises a heated wire, the Wheatstone bridge sensor yielding a signal proportional to a change in temperature of the heated wire in response to a change in flow properties of the CMP polish slurry;
   a frequency-domain transform device for forming a frequency-domain transform of the signal; and,
   an output device for receiving and displaying the frequency-domain transform of the signal.

2. The system of claim 1, further comprising an amplifier for amplifying the signal prior to forming the frequency-domain transform of the signal.

3. The system of claim 1, wherein the frequency-domain transform of the signal is a Fast Fourier Transform (FFT).

4. The system of claim 1, wherein the Wheatstone bridge sensor is sensitive to changes in the CMP slurry flow properties occurring over a timescale on the order of milliseconds.

5. The system of claim 1, wherein the frequency-domain transform device comprises a programmed computing device.

* * * * *